(12) United States Patent
Ruoslahti et al.

(10) Patent No.: US 6,303,573 B1
(45) Date of Patent: Oct. 16, 2001

(54) HEART HOMING PEPTIDES AND METHODS OF USING SAME

(75) Inventors: Erkki Ruoslahti, Rancho Santa Fe; Deidre A. MacKenna, San Diego, both of CA (US)

(73) Assignee: The Burnham Institute, La Jolla, CA (US)

(*) Notice: Subject to any disclaimer, the term of this patent is extended or adjusted under 35 U.S.C. 154(b) by 0 days.

(21) Appl. No.: 09/326,718

(22) Filed: Jun. 7, 1999

(51) Int. Cl.$^7$ ..................................................... A61K 38/00
(52) U.S. Cl. .................................. 514/12; 514/2; 514/14; 514/16; 514/21; 530/300; 530/324; 530/327; 530/328; 530/329; 424/185.1
(58) Field of Search ................................. 514/12, 14, 16, 514/2, 21; 530/300, 324, 327, 328, 329; 424/185.1

(56) References Cited

U.S. PATENT DOCUMENTS 5,622,699 * 4/1997 Ruoslahti et al. ................... 424/93.6

FOREIGN PATENT DOCUMENTS

WO 97/10507    3/1997   (WO).

OTHER PUBLICATIONS

Deckert et al. *Nature,* vol. 392 (6674) 1998, pp. 353–358.*
Somanchi et al., *Can J. Bot.,* vol. 76, No. 6, 1998, pp. 1003–1009.*
Rajotte et al., "Molecular Heterogeneity of the Vascular Endothelium Revealed by in Vivo Phage Display," *J. Clin. Invest.,* 102:430–437 (1998).
Billups et al., "Expression of E–selectin mRNA during ischemia/reperfusion injury," *J. Lab. Clin. Med.* 125:626–633 (1995).
Bowles et al., "Prospects for adenovirus–mediated gene therapy of inherited diseases of the myocardium," *Cardiovascular Research* 35:422–430 (1997).
Giordano et al., "Intracoronary gene transfer of fibroblast growth factor–5 increases blood flow and contractile function in an ischemic region of the heart," *Nature Medicine* 2:534–539 (1996).
Harada et al., "Vascular endothelial growth factor administration in chronic myocardial ischemia," *American Journal of Physiol.* 270:H1791–H1802 (1996).
Herskowitz et al., "Cytokine mRNA Expression in Postischemic/Reperfused Myocardium," *Am. J. Pathol.* 146:419–428 (1995).
Indolfi and Chiariello, "Gene therapy for cardiovascular disorders," *Cardiologia* 43:365–373 (1998).
Isner et al., "Clinical evidence of angiogenesis after arterial gene transfer of phVEGF$_{165}$ in patient with ischemic limb," *The Lancet* 348:370–374 (1996).
Knight and Fox, "The Viscious Circle of Ischemic Left Ventrical Dysfunction," *Am. J. Cardiol.* 75:10E–15E (1995).

Korthus et al., "Role of Neutrophil–Endothelial cell Adhesion in Inflammatory Disorders," *J. Crit. Care* 9(1):47–71 (1994).
Kukielka et al., "Role of early reperfusion in the induction of adhesion molecules and cytokines in previously ischemic myocardium," *Molec. And Cell Biochem.* 147:5–12 (1995).
Lefer and Lefer, "Pharmacology of the Endothelium in Ischemia–Reperfusion and Circulatory Shock," *Annu. Rev. Pharmacol. Toxicol.* 33:71–90 (1993).
Ma et al., "Coronary Endothelial and Cardiac Protective Effects of a Monoclonal Antibody to Intercellular Adhesion Molecule–1 in Myocardial Ischemia and Reperfusion," *Circulation* 86:937–946 (1992).
Marche et al., "Pharmacologic treatment of atherosclerosis: beyond lipid–lowering therapy," *International Journal of Cardiology* 62:S17–S22 (1997).
Meredith et al., "Role of Endothelium in Ischemic Coronary Syndromes," *Am. J. Cardiol.* 72:27C–32C (1993).
Pasqualini and Ruoslahti, "Organ targeting in vivo using phage display peptide libraries," *Nature* 380:364–366 (1996).
Rader, "Gene therapy for a therosclerosis," *Int. J. Clin. Lab. Res.* 27:35–43 (1997).
Scalia et al., "Myocardial protection by N,N,N–trimethylsphingosine in ischemia reperfusion injury is mediated by inhibition of P–selectin," *J. Leukoc. Biol.* 59:317–324 (1996).
Schachter, "Calcium antagonists and atherosclerosis," *International Journal of Cardiology* 62:S9–S15 (1997).
Schachter, "Vascular smooth muscle cell migration, atherosclerosis, and calcium channel blockers," *International Journal of Cardiology* 62:S85–S90 (1997).
Seccombe and Schaff, "Coronary Artery Endothelial Function After Myocardial Ischemia and Reperfusion," *Ann. Thorac. Surg.* 60:778–788 (1995).
Simari and Nabel, "Genetic Therapy," *Semin. Intervent. Cardiol.* 1:77–83 (1996).
Trost et al., "Protection Against Myocardial Dysfunction After a Brief Ischemic Period in Transgenic Mice Expressing Inducible Heat Shock Protein 70," *J. Clin. Invest.* 101:855–862 (1998).
Weyrich et al., "Time course of coronary vascular endothelial adhesion molecule expression during reperfusion of the ischemic feline myocardium," *J. Leukoc. Biol.* 57:45–55 (1995).
Youker et al., "Molecular Evidence for Induction of Intracellular Adhesion Molecule–1 in the Viable border Zone Associated with Ischemia–Reperfusion Injury of the Dog Heart," *Circulation* 89:2736–2746 (1994).

* cited by examiner

*Primary Examiner*—Avis M. Davenport
(74) *Attorney, Agent, or Firm*—Campbell & Flores LLP (57) ABSTRACT

The present invention provides a heart homing peptide that contains the amino acid sequence GGGVFWQ (SEQ ID NO: 2); HGRVRPH (SEQ ID NO: 3); VVLVTSS (SEQ ID NO: 4); CLHRGNSC (SEQ ID NO: 9); or CRSWNKAD-NRSC (SEQ ID NO: 10) and further provides conjugates in which a heart homing peptide is linked to a moiety such as a therapeutic agent. The conjugates of the invention are useful for treating cardiovascular diseases such as atherosclerosis and restenosis.

27 Claims, 2 Drawing Sheets

HEART HOMING PEPTIDES AND METHODS OF USING SAME

This invention was made with government support under grant numbers CA 74238 and CA 30199 awarded by the National Institutes of Health.

BACKGROUND OF THE INVENTION

1. Field of the Invention

The present invention relates generally to the fields of molecular medicine and drug and gene delivery and, more specifically, to novel compositions for treating cardiovascular disease.

2. Background Information

The term atherosclerosis is used to describe thickening and inelasticity of vessel walls or arteries as a consequence of atheroma. Atherosclerosis and its sequelae constitute the most common and important cause of disease and death in the western world, accounting for 50% of all deaths in the west.

In normal hearts, vessel walls are composed of an endothelial cell lining that is tightly juxtaposed to a medial layer of vascular smooth muscle cells with an over layer of connective tissue. The endothelial cell lining is ideally situated at the interface between the blood and the vessel wall to transduce signals, with endothelial cells controlling the homeostatic balance of the vessel through the production of factors regulating vessel tone, coagulation state, cell growth, cell death, and leukocyte trafficking. Vascular smooth muscle cells maintain the contractile tone of the blood vessel in response to vasoactive agents and release cytokines and other growth factors. In conjunction with fibroblasts, the smooth muscle cells produce extracellular matrix proteins and proteases that determine vessel structure. Occlusive vascular disease, the most common form of which is atherosclerosis, is characterized by an abnormal accumulation of vascular smooth muscle cells, inflammatory cells, and extracellular matrix proteins within the intimal space between the endothelial lining and the medial layer (neointima formation).

Therapies for atherosclerosis generally prevent, arrest or reverse the process of neointima formation or stimulate new blood vessel formation (angiogenesis). It is rare, however, that a drug or other agent for treatment of atherosclerosis targets only coronary vessels. More commonly, systemic administration results in undesirable side effects due, for example, to generalized toxic effects throughout the entire body. For example, vascular endothelial growth factor (VEGF), a key regulator of angiogenesis that stimulates endothelial cell proliferation, promotes the formation of new vessels, thereby increasing blood flow to ischemic tissue and relieving vascular disease. However, VEGF also can promote nonspecific mitogenesis and potentiate angiogenesis-driven diseases such as diabetic retinopathy, and certain tumors. Similarly, systemic administration of the angiogenic stimulator fibroblast growth factor can cause severe side effects due to its lack of specificity for heart tissue. Unfortunately, such side effects, including repetitive episodes of hypertension, limit the utility of this therapy.

As the internal lining of blood vessels, the endothelium is the first cell type encountered by a circulating therapeutic substance. Endothelial cells therefore provide a target for selectively directing a therapeutic substance to cardiac tissue. Such selective targeting of a therapeutic agent to cardiac endothelium would reduce or eliminate the risk of unwanted side effects such as systemic toxicity or malignant transformation. Selective targeting of a therapeutic substance to cardiac endothelium also would effect a high local concentration of the substance, thereby reducing the dosage required for effective treatment.

Thus, a need exists to identify molecules that selectively bind to cardiac endothelium in vivo. Such molecules would be particularly useful for selectively targeting therapeutic agents to the heart for treatment of atherosclerosis. The present invention satisfies this need and provides related advantages as well.

SUMMARY OF THE INVENTION

The present invention provides an isolated heart homing peptide that selectively homes to cardiac tissue. An isolated heart homing peptide of the invention can contain, for example, the amino acid sequence GGGVFWQ (SEQ ID NO: 2); HGRVRPH (SEQ ID NO: 3); VVLVTSS (SEQ ID NO: 4); CLHRGNSC (SEQ ID NO: 9); or CRSWNKAD-NRSC (SEQ ID NO: 10), or a functionally equivalent modification thereof. An isolated heart homing peptide of the invention can have, for example, a length of less than forty amino acids or a length of less than fifteen amino acids.

Also provided by the invention is a conjugate composed of a heart homing peptide linked to a moiety, where the heart homing peptide contains the amino acid sequence GGGVFWQ (SEQ ID NO: 2); HGRVRPH (SEQ ID NO: 3); VVLVTSS (SEQ ID NO: 4); CLHRGNSC (SEQ ID NO: 9); or CRSWNKADNRSC (SEQ ID NO: 10), or a functionally equivalent modification thereof. In a conjugate of the invention, the moiety can be, for example, a therapeutic agent, detectable agent or tag. Exemplary therapeutic agents are provided herein as vascular endothelial growth factor (VEGF) and fibroblast growth factor (FGF).

The present invention further provides a method of treating a cardiovascular disease in a subject by administering a conjugate that contains a heart homing peptide linked to a therapeutic agent, where the heart homing peptide contains the amino acid sequence GGGVFWQ (SEQ ID NO: 2); HGRVRPH (SEQ ID NO: 3); VVLVTSS (SEQ ID NO: 4); CLHRGNSC (SEQ ID NO: or CRSWNKADNRSC (SEQ ID NO: 10), or a functionally equivalent modification thereof. The methods of the invention are useful for treating a variety of cardiovascular diseases including atherosclerosis and restenosis.

Also provided by the invention is an isolated peptide that selectively homes to ischemic tissue. Such a peptide, referred to herein as an ischemic tissue selective peptide, can contain, for example, the amino acid sequence CRSWNKADNRSC (SEQ ID NO: 10), or a functionally equivalent modification thereof. In one embodiment, the isolated ischemic tissue selective peptide is not an antibody or antigen-binding fragment thereof. In other embodiments, the ischemic tissue selective peptide has a length of less than forty amino acids or a length of less than fifteen amino acids. An ischemic tissue selective peptide of the invention can be useful in the form of a conjugate to selectively deliver a linked moiety to ischemic tissue.

The invention also provides methods of treating ischemic disease in a subject. The methods involve administering a conjugate including an ischemic tissue selective peptide that selectively homes to ischemic tissue, where the peptide is linked to a moiety.

BRIEF DESCRIPTION OF THE DRAWINGS

FIG. 1 shows the results of homing of individual phage clones to normal cardiac vasculature. Individual phage ($5 \times 10^9$ TU) were injected intravenously and allowed to circulate for 5 minutes prior to perfusion of the vasculature and harvesting of the heart and brain. The number of phage recovered from the heart (per gram) was normalized by the number of phage recovered from the brain (per gram). Fd-tet was a phage without any additional peptide insert. Several different phage from the $X_7$ (SEQ ID NO: 1) linear peptide library (GGGVFWQ (SEQ ID NO: 2; D7), HGRVRPH (SEQ ID NO: 3; D33), VVLVTSS (SEQ ID NO: 4; D35), QGRLYNY (SEQ ID NO: 5; D38), AWGLASY (SEQ ID NO: 6; D40), RSMPLLS (SEQ ID NO: 7; D24), and RPGRLNG (SEQ ID NO: 8; D17)) were each tested in six separate animals. The data shown are the logarithmic means and logarithmic standard errors of the multiple experiments.

FIG. 2 shows the results of homing of individual phage clones to normal or ischemic vasculature. Individual phage obtained from screening in ischemic-reperfused hearts were injected at $5 \times 10^9$ TU intravenously into normal animals (open squares) or animals subject to 30 minutes myocardial ischemia by occlusion of the left anterior descending (LAD) coronary artery followed by 30 minutes reperfusion (closed circles). Phage were allowed to circulate for 5 minutes prior to perfusion of the vasculature and harvesting of the heart and brain. The number of phage recovered from the heart (per gram) was normalized by the number of phage recovered from the brain (per gram). Fd-tet was a phage without any additional peptide insert. Several different phage from cyclic peptide libraries (CLHRGNSC(SEQ ID NO: 9; IL10); CRSWNKADNRSC (SEQ ID NO: 10; R13); CSMYFQRC (SEQ ID NO: 11; I12); and CNASILRNGQNC (SEQ ID NO: 12; I1)) were each tested in 6 to 7 normal and ischemia-reperfusion injured animals. The data shown are the logarithmic means and logarithmic standard errors of the multiple experiments.

DETAILED DESCRIPTION OF THE INVENTION

The present invention provides an isolated heart homing peptide that selectively homes to cardiac tissue. Such an isolated heart homing peptide can contain, for example, the amino acid sequence GGGVFWQ (SEQ ID NO: 2); HGRVRPH (SEQ ID NO: 3); VVLVTSS (SEQ ID NO: 4); CLHRGNSC (SEQ ID NO: 9); or CRSWNKADNRSC (SEQ ID NO: 10), or a functionally equivalent modification thereof. A heart homing peptide of the invention selectively homes to cardiac tissue and can be useful in the form of a conjugate for selectively targeting a systemically administered therapeutic agent to cardiac tissue. Such selective targeting of a therapeutic agent increases the effective amount of an agent delivered to the heart while reducing the likelihood that the agent will have an adverse effect on other organs. For example, as disclosed herein, in vivo panning identified peptides GGGVFWQ (SEQ ID NO: 2), HGRVRPH (SEQ ID NO: 3) VVLVTSS (SEQ ID NO: 4) and CLHRGNSC (SEQ ID NO: 9) as selectively binding to normal heart in preference to control brain following administration through the jugular vein (see Example I). Furthermore, peptide CRSWNKADNRSC (SEQ ID NO: 10) was enriched five-fold for binding to heart injured by ischemia-reperfusion injury as compared to brain (see Example II).

Thus, the heart homing peptides of the invention are useful in the form of conjugates for targeting a linked moiety to the heart. Such a moiety can be a therapeutic agent such as a viral gene therapy vector, drug or therapeutic protein; a detectable or imaging agent such as a radionuclide; or a tag such as biotin. A heart homing peptide of the invention can be used, for example, to deliver an agent for prophylactic treatment of cardiovascular disease or to deliver a therapeutic agent selectively to ischemic tissue. As further disclosed herein, a heart homing peptide of the invention can be used to detect or visualize the heart or to isolate an endothelial target molecule that binds the heart homing peptide.

The heart homing peptides of the invention selectively home to cardiac tissue. As used herein, the term "selectively home," when used in reference to a heart homing peptide, means a peptide that selectively binds to normal cardiac tissue or pathologic cardiac tissue, such as ischemic tissue, in preference to other non-cardiac tissues of the body. In general, a heart homing peptide of the invention is characterized by at least a two-fold greater selective binding of the peptide to cardiac tissue as compared to a control tissue such as brain (see Examples I and II).

The term "homing peptide," as used herein, refers to a heart homing peptide, an ischemic tissue selective peptide or a peptide that selectively homes to limb vasculature, described hereinbelow.

Selective homing can be demonstrated by determining if binding of a homing peptide to the selected tissue is relatively specific. For example, the amount of a particular heart homing peptide in cardiac tissue can be compared to the amount of the heart homing peptide that accumulates in a control organ or tissue. For example, phage expressing the peptides SEQ ID NOS: 2, 3, 4 and 9 were at least two-fold enriched in normal heart as compared to control brain tissue (see Example I). Phage expressing the peptide sequence GGGVFWQ (SEQ ID NO: 2) accumulated 5-fold more in normal heart than in the brain (see Table 2). Selective homing also can be demonstrated by showing that peptides that home to the heart, as identified by one round of in vivo panning, are enriched in one or more subsequent rounds of in vivo panning.

Alterations in surface expression in the vasculature have been extensively studied in ischemia-reperfusion injury (Knight and Fox, *Am. J. Cardiol.* 75:10E–15E (1995); Meredith et al., *Am. J. Cardiol.* 72:27C–32C (1993); and Korthuis et al., *J. Crit. Care* 9(1):47–71 (1994)). In several organ systems including the heart, restoration of flow to a previously ischemic region induces an array of responses (Lefer and Lefer, *Annu. Rev. Pharmacol. Toxicol.* 33:71–90

(1993); Seccombe and Schaff, *Ann. Thorac. Surg.* 60:778–788 (1995); and Herskowitz et al., *Am. J. Pathol.* 146:419–428 (1995)). An initial burst of oxygen free radicals activate and stiffen the endothelium. Endothelium-derived relaxation factor, now known to be nitric oxide (NO), levels decrease causing localized vasoconstriction. Endothelial expression of several cell adhesion molecules including PECAM, ICAM and VCAM increases in a time-dependent manner and enhances leukocyte adhesion (Billups et al., *J. Lab. Clin. Med.* 125:626–633 (1995); Kukielka et al., *Molec. And Cell Biochem.* 147:5–12 (1995); Scalia et al.,*J. Leukoc. Biol.* 59:317–324 (1996); Weyrich et al., *Leukoc. Biol.* 57:45–55 (1995); and Youker et al., *Circulation* 89:2736–2746 (1994)). As a consequence, reperfusion causes an inflammatory response and neutrophil recruitment that can accelerate the cell death associated with the ischemic insult itself.

Molecules selectively expressed in ischemic vasculature provide targets for peptides that can bind selectively to ischemic tissue in preference to other tissues. As disclosed herein, peptide CRSWNKADNRSC (SEQ ID NO: 10) showed 5-fold enrichment for ischemic heart tissue as compared to brain, but did not target normal heart (Example II; Table 2). Furthermore, phage bearing peptide SEQ ID NO: 10 preferentially homed to the ischemic left ventricle as compared to the uninjured right ventricle. These results indicate that molecules such as peptide SEQ ID NO: 10 can selectively accumulate in ischemic tissue such as ischemic cardiac tissue in preference to healthy tissue. Peptides that selectively home to ischemic tissue, and conjugates in which such a peptide is linked to an imaging or therapeutic agent, can be particularly useful for detecting and treating diseases of ischemic tissues, including ischemic heart disease.

Thus, the invention also provides an isolated peptide that selectively homes to ischemic tissue. Such a peptide, referred to herein as an ischemic tissue selective peptide, can be, for example, a peptide containing the amino acid sequence CRSWNKADNRSC (SEQ ID NO: 10), or a functionally equivalent modification thereof. In one embodiment, the isolated ischemic tissue selective peptide is not an antibody or antigen-binding fragment thereof. In other embodiments, the ischemic tissue selective peptide has a length of less than forty amino acids or a length of less than fifteen amino acids.

In another embodiment, the invention provides an ischemic tissue selective peptide containing the sequence RSW, SWN, WNK, NKA, KAD, AND, DNR, or NRS. Such a peptide can be linear or cyclic and can have, for example a length of less than forty amino acids or a length of less than fifteen amino acids.

As used herein, the term "ischemic tissue" means a tissue damaged by temporary or permanent interruption of blood flow to the arterial vasculature. Such an ischemic tissue, which receives a reduced blood supply, generally is deprived of a lack of oxygen, the supply of substrates for metabolic and synthetic processes and a means of removing waste products such as acid metabolic products. Mild, chronic local ischemia typically results in atrophied tissue, while acute ischemia produces ischemic necrosis, also termed infarction. Examples of ischemic tissues include ischemic myocardium and watershed lesions, which are areas of ischemia in the brain and colon at the junction of territories supplied by two arteries. Exemplary ischemic tissues also include infarcted tissues such as myocardial infarcts or infarcts of the brain; retina; whole limbs; kidneys; spleen; lung and bones (see, for example, Majno and Joris, *Cells, Tissues and Disease: Principles of General Patholoay*, Chapter 24, Blackwell Science, Inc., Cambridge (1996); *Dorland's Illustrated Medical Dictionary*, 28th Edition, W.B. Saunders Company, Philadelphia (1994).

As used herein, the term "selectively homes," when used in reference to ischemic tissue, means that the peptide selectively binds to one or more ischemic tissues in preference to other healthy tissues. In general, a peptide that selectively binds to ischemic tissue is characterized by at least a two-fold greater selective binding of the peptide to one or more ischemic tissues as compared to tissue that is not ischemic. Such an ischemic tissue selective peptide can preferentially bind, for example, to ischemic brain, retina, whole limbs, kidneys, spleen, lung, bones or heart, or any combination thereof. Phage bearing SEQ ID NO: 10, for example, accumulated in ischemic heart five-fold more than in normal brain (see Example II). Methods for determining selective binding of a homing peptide are exemplified herein and described hereinabove.

The present invention also provides a peptide that selectively homes to peripheral vasculature of the limbs. Such a peptide selectively binds to the vasculature of the arms or legs in preference to other tissues. In general, a peptide that selectively homes to peripheral vasculature of the limbs is characterized by at least a two-fold greater selective binding of the peptide to limb vasculature as compared to other vasculature or tissue. A peptide that selectively homes to peripheral vasculature of the limbs can contain, for example, the amino acid sequence GGGVFWQ (SEQ ID NO: 2); HGRVRPH (SEQ ID NO: 3); VVLVTSS (SEQ ID NO: 4); CLHRGNSC (SEQ ID NO: 9) or CRSWNKADNRSC (SEQ ID NO: 10), or a functionally equivalent modification thereof.

As used herein, the term "peptide" is used broadly to mean a linear, cyclic or branched peptide, peptoid, peptidomimetic, or the like. With respect to the heart homing peptides of the invention, peptidomimetics, which include chemically modified peptides, peptide-like molecules containing non-naturally occurring amino acids, peptoids and the like, have the binding activity of the heart homing peptide upon which the peptidomimetic is derived (see, for example, "Burger's Medicinal Chemistry and Drug Discovery" 5th ed., vols. 1 to 3 (ed. M. E. Wolff; Wiley Interscience 1995)). Peptidomimetics provide various advantages over peptides, and are particularly useful for oral administration since they can be stable when administered to a subject during passage throughout the digestive tract.

The peptides of the invention are provided in isolated form. As used herein in reference to a homing peptide of the invention, the term "isolated" means a peptide that is in a form that is relatively free from unrelated peptides as well as contaminating polypeptides, lipids, nucleic acids and other cellular material that normally are associated with the peptide in a cell or that are associated with the peptide in a library. An isolated peptide can be a pool containing a small number of related or unrelated peptides, provided that the pool contains at most fifteen peptides of different amino acid sequence, for example, five or ten peptides of different amino acid sequence.

A peptide of the invention also can be provided in a form that is "substantially pure." As used herein in reference to a peptide of the invention, the term "substantially pure" means a peptide preparation that is essentially homogeneous, containing molecules having a single amino acid sequence.

A homing peptide of the invention can be a relatively short peptide of less than eight, ten, 12, 15, 20, 25, 30, 35 or 40 amino acids. A homing peptide of the invention also can have a length of less than 50, 100, 150 or 200 amino acids. A homing peptide of the invention also can maintain its homing capability in the context of a significantly longer polypeptide sequence. Thus, a heart homing peptide or ischemic tissue selective peptide of the invention can have a length of more than 20 amino acids, for example, more than 40, 60, 80, 100, 200 or 400 amino acids. In one embodiment, a homing peptide of the invention is not an antibody or antigen-binding fragment thereof, which is an art-recognized term that refers to a peptide or polypeptide containing one or more complementarity determining regions (CDRs). See, for example, Borrabaeck, *Antibody Engineering* 2nd Edition, Oxford University Press, New York (1995).

As used herein in reference to a homing peptide of the invention, the term "functionally equivalent modification" means a molecule having a similar, non-identical sequence that is considered by those skilled in the art to have the same function in regard to selective homing. For example, a functionally equivalent modification of the heart homing peptide containing the amino acid sequence GGGVFQW (SEQ ID NO: 2) contains an amino acid sequence that is similar but non-identical to SEQ ID NO: 2 and that is functionally equivalent due to an ability to selectively home to cardiac tissue. Such a functionally equivalent modification can be one or more amino acid additions, deletions or substitutions relative to SEQ ID NO: 2, provided that the peptide retains the ability to selective home to cardiac tissue. Similarly, a functionally equivalent modification of an ischemic tissue selective peptide such as SEQ ID NO: 10 contains an amino acid sequence that is similar but non-identical to SEQ ID NO: 10 and that is functionally equivalent due to an ability to selectively home to one or more ischemic tissues.

A functionally equivalent modification can be, for example, one or two amino acid additions or substitutions relative to the reference peptide sequence. In one embodiment, such a functionally equivalent modification, can be up to two amino acid substitutions, which can be conservative or non-conservative. In another embodiment, such a functionally equivalent modification is a single amino acid substitution, which is conservative or non-conservative. In a further embodiment, the functionally equivalent modification can be up to two conservative amino acid substitutions, for example, a single conservative amino acid substitution.

One skilled in the art understands that a conservative substitution is the replacement of a first amino acid with a second amino acid having similar biochemical properties. For example, a first nonpolar amino acid can be conservatively substituted with a second (non-identical) nonpolar amino acid such as alanine, valine, leucine, isoleucine, proline, methionine, phenylalanine or tryptophan. Similarly, a first uncharged polar amino acid can be conservatively substituted with a second uncharged polar amino acid such as glycine, serine, threonine, cysteine, tyrosine, asparagine or glutamine. In addition, a first negatively charged amino acid can be conservatively substituted with a second negatively charged amino acid such as aspartic acid or glutamic acid. In the same way, a first positively charged amino acid can be conservatively substituted with a second positively charged amino acid such as lysine, arginine or histidine. Non-conservative substitutions, which also are encompassed by the invention, involve the replacement of an amino acid of one class, for example, a nonpolar residue, with an amino acid of a second class, for example, a polar or charged residue.

Therefore, it is understood that limited modifications can be made without destroying the homing activity of a peptide of the invention. These functionally equivalent modifications can be deliberate, as through site-directed mutagenesis, or can be accidental such as through mutation in hosts harboring an encoding nucleic acid. One skilled in the art also understands that minor modifications of primary amino acid sequence can result in peptides which have enhanced function as compared to the parent homing peptide, for example, an enhanced selectivity for normal cardiac tissue as compared to other tissues or selectivity for a second tissue in addition to cardiac tissue. All such modified polypeptides are included in the definition of a "functionally equivalent modification."

One skilled in the art understands that a peptide of the invention can have an inherent biological property, such that administration of the peptide provides a direct biological effect. For example, a heart homing peptide can be sufficiently similar to a naturally occurring ligand for the target molecule that the homing peptide mimics the activity of the natural ligand or acts as an antagonist of the natural ligand. Such a heart homing peptide can be useful as a therapeutic agent having the activity of the natural ligand or as a therapeutic agent that inhibits the activity of the natural ligand. Such inherent biological activity can be identified by contacting cardiac cells with a heart homing peptide of the invention and examining the cells for evidence of a biological effect.

Exemplified herein are various heart homing peptides such as GGGVFWQ (SEQ ID NO: 2); HGRVRPH (SEQ ID NO: 3); VVLVTSS (SEQ ID NO: 4); CLHRGNSC (SEQ ID NO: 9); or CRSWNKADNRSC (SEQ ID NO: 10). Also exemplified herein is an ischemic tissue selective peptide, CRSWNKADNRSC (SEQ ID NO: 10). Additional heart homing peptides or ischemic tissue selective peptides can be identified using in vivo panning, which is a method of screening a library by administering the library to a subject and identifying a peptide that selectively homes to cardiac tissue or ischemic tissue (U.S. Pat. No. 5,622,699, supra, 1997). The term "administering to a subject", when used in referring to a library of peptides or a portion of such library, is used in its broadest sense to mean that the library is delivered to a selected tissue in the subject, which, generally, is a vertebrate, particularly a mammal such as a human. Libraries of molecules can be administered by any route or means of administration, such as intravenously, intramuscularly, orally, optically, ocularly, intraperitoneally, nasally, vaginally, rectally, into the uterus, into a chamber of the eye, into the central or peripheral nervous system, by inhalation, by topical administration, or by injection into any normal organ or tissue or into a pathological region, particularly into the circulatory system of the tissue.

As used herein, the term "library" means a collection of peptides. A library can contain a few or a large number of different peptides, varying from about 50 to about $10^{15}$ molecules or more. The chemical structure of the peptides of a library can be related to each other or be diverse. If desired, the peptides constituting the library can be linked to a common or unique tag, which can facilitate recovery and/or identification of the homing peptide.

Methods for preparing libraries containing diverse populations of peptides, peptoids and peptidomimetics are well known in the art and various libraries are commercially available (see, for example, Ecker and Crooke, *Biotechnology* 13:351–360 (1995), and Blondelle et al., *Trends Anal. Chem.* 14:83–92 (1995), and the references cited therein, each of which is incorporated herein by reference; see, also, Goodman and Ro, *Peptidomimetics for Drug Design*, in "Burger's Medicinal Chemistry and Drug Discovery" Vol. 1 (ed. M. E. Wolff; John Wiley & Sons 1995), pages 803–861, and Gordon et al., *J. Med. Chem.* 37:1385–1401 (1994), each of which is incorporated herein by reference). One skilled in the art understands that a peptide can be produced in vitro directly or can be expressed from a nucleic acid, which can be produced in vitro. Methods of synthetic peptide and nucleic acid chemistry are well known in the art.

A library of peptide molecules also can be produced, for example, by constructing a cDNA expression library from mRNA collected from a tissue of interest. Methods for producing such libraries are well known in the art (see, for example, Sambrook et al., *Molecular Cloning: A laboratory manual* (Cold Spring Harbor Laboratory Press 1989), which is incorporated herein by reference). Preferably, a peptide encoded by the cDNA is expressed on the surface of a cell or a virus containing the cDNA.

As disclosed herein, in vivo panning for the purpose of identifying a homing peptide includes the steps of administering a library to a subject, collecting an organ or tissue sample and identifying a homing peptide using various methods well known in the art. Generally, the presence of a homing peptide in a collected organ or tissue is identified based on one or more characteristics common to the peptides present in the library, then the structure of a particular homing peptide can be determined.

A highly sensitive detection method such as mass spectrometry (MS), either alone or in combination with a method such as gas chromatography (GC), can be used to identify homing peptides that are closely related even when present in small amounts in a selected organ or tissue. If desired, the selected cardiac tissue or ischemic tissue can be processed using a method such as HPLC, which can be used to obtain an enriched fraction of peptides having a defined range of molecular weights or polarity or the like from a complex mixture. The enriched fraction of peptides then can be further analyzed for the purposes of identifying homing peptides. Conditions for HPLC will depend on the structure of the particular molecule and can be optimized by those skilled in the art based on knowledge of the molecule.

The members of a peptide library can be tagged, which can facilitate recovery or identification of the heart homing peptide or ischemic tissue selective peptide. As used herein, the term "tag" means a physical, chemical or biological moiety such as a plastic or metallic microbead, an oligonucleotide or a bacteriophage, respectively, that is linked to a member of the library. Methods for tagging a peptide are well known in the art (Hermanson, *Bioconjugate Techniques*, (Academic Press 1996), which is incorporated herein by reference). The link between a peptide and a tag can be a covalent or a non-covalent bond and, if desired, the link can be selectively cleavable from the peptide.

A tag can be a shared tag, which is a physical, chemical or biological moiety that is common to each peptide in a library. A shared tag can be used to identify the presence of a peptide of the library in a sample or to substantially isolate the homing peptides from a sample following in vivo panning. A shared tag such as biotin, for example, can be used to isolate a linked peptide from cardiac tissue or ischemic tissue using streptavidin affinity chromatography. The presence of the homing peptide also can be detected by binding with a labeled streptavidin. A shared tag also can be an antigen such an the hemagglutinin antigen, which, when linked to each peptide in a library, allows the use of an antibody specific for the hemagglutinin antigen to substantially isolate homing peptides from the selected cardiac tissue or ischemic tissue. Furthermore, peptide can be linked to a hapten such as 4-ethoxy-methylene-2-phenyl-2-oxazoline-5-one (phOx), which can be bound by an anti-phOx antibody linked to a magnetic bead as a means to recover the homing peptide. Methods for purifying phOx labeled conjugates are known in the art and the materials for performing these procedures are commercially available (Invitrogen, La Jolla CA; Promega Corp., Madison Wiss.).

A shared tag also can be a nucleic acid sequence that can be used to identify the presence of peptides of the library in a sample or to substantially isolate peptides of a library from a sample. For example, each of the molecules of a library can be linked to the same selected nucleotide sequence, which constitutes the shared tag. An affinity column containing a nucleotide sequence that is complementary to the shared tag then can be used to isolate the homing peptides from an organ or tissue sample by hybridizing to the shared tag linked to the molecules. A nucleotide sequence complementary to a portion of the shared tag also can be used as a PCR primer such that the presence of peptides containing the shared tag can be identified in a sample by PCR.

A tag also can be a specific or a unique tag, which is a physical, chemical or biological tag that is linked to a peptide in a library and that is unique for the particular peptide. A specific tag is particularly useful if it is readily identifiable. A nucleotide sequence that is unique for a particular molecule of a library is an example of a specific tag, for example, a unique oligonucleotide tag linked to each peptide of a library (see, for example, Brenner and Lerner, *Proc. Natl. Acad. Sci. USA* 89:5381–5383 (1992), which is incorporated herein by reference). Upon homing to cardiac tissue or ischemic tissue, the homing peptide can be identified by determining the sequence of the unique oligonucleotide tag using, for example, PCR (see, for example, Erlich, *PCR Technology: Principles and Applications for DNA Amplification* (Stockton Press 1989), which is incorporated herein by reference). Similarly, the nucleic acid sequence encoding a peptide displayed on a phage is another example of a specific nucleic acid tag, since sequencing of the nucleic acid identifies the amino acid sequence of the expressed peptide (see Example I).

A shared tag and specific tag, in combination, can be particularly useful for isolating and identifying a homing peptide when the homing peptide is present in minute quantities. For example, each peptide of a library can be linked to an oligonucleotide tag which contains two portions; an internal unique nucleotide sequence tag and shared flanking 5' and 31' nucleotide tags that serve as primer binding sites for use in PCR. Each molecule, therefore, contains an oligonucleotide tag having a unique portion to identify the homing molecule and a shared portion to provide PCR primer binding sites. Such a tagged molecule, upon homing to a selected organ or tissue, can be identified by performing PCR using primers that hybridize to the shared flanking 5' and 3' nucleotide tags, then performing DNA sequencing to determine the nucleotide sequence of the internal unique sequence tag. The PCR product can be sequenced directly using one of the PCR primers or the PCR product can be cloned into a vector and the DNA sequence determined by routine methods well known in the art.

Various other combinations of shared and unique tags can be used. For example, each of the peptides in a library can be linked to a specific nucleotide sequence tag (see, for example, Brenner and Lerner, supra, 1992), which also contains a shared 3' nucleotide sequence that can be a primer binding site for use in PCR, and can be further linked to a shared tag such as biotin. Upon homing to cardiac tissue or ischemic tissue, the particular homing peptide can be substantially isolated from an organ or tissue sample based on the biotin tag. The isolated homing peptides can then be identified, for example, by PCR based DNA sequencing of the specific tag using the shared 3' nucleotide sequence of the nucleotide tag as a primer binding site.

As disclosed herein, bacteriophage linked to a heart homing peptide selectively accumulated in the heart. For example, phage expressing the peptide GGGVFWQ (SEQ ID NO: 2) were selectively enriched in normal heart five-fold more than in brain, and phage expressing the peptide CRSWNKADNRSC (SEQ ID NO: 10) were selectively enriched in ischemic heart five-fold more than in brain (see Example I). These results indicate that a heart homing peptide of the invention can be linked to a bacteriophage or another moiety in order to direct the moiety to the heart in preference to other tissues. Thus, the present invention provides conjugates, in which a heart homing peptide is linked to a moiety. Such conjugates are useful for directing a moiety to cardiac tissue and can be used to treat a variety of cardiovascular diseases such as atherosclerosis and restenosis (see below).

The present invention provides conjugates containing a heart homing peptide linked to a moiety, where the heart homing peptide contains the amino acid sequence GGGVFWQ (SEQ ID NO: 2); HGRVRPH (SEQ ID NO: 3); VVLVTSS (SEQ ID NO: 4); CLHRGNSC (SEQ ID NO: 9); or CRSWNKADNRSC (SEQ ID NO: 10), or a functionally equivalent modification thereof. In a conjugate of the invention, the moiety can be, for example, a therapeutic agent, detectable agent or tag. Exemplary therapeutic agents are provided herein as vascular endothelial growth factor (VEGF) and fibroblast growth factor (FGF).

As used herein, the term "moiety" is used broadly to mean a physical, chemical, or biological material that can be linked to a homing peptide of the invention and generally imparts a biologically useful function to the homing peptide. A moiety can be any natural or nonnatural material such as an organic chemical, radionuclide, nucleic acid molecule or oligonucleotide, polypeptide or peptide. A moiety can be, for example, a therapeutic agent; diagnostic agent or imaging agent; or a tag or insoluble support. These and other moieties known in the art can be used in a conjugate of the invention, and in a method of the invention, as disclosed hereinbelow.

Useful moieties include viral gene therapy vectors; viruses; nucleic acid molecules and oligonucleotides; polypeptides and peptides; small molecule drugs; cells; liposomes; microcapsules and microspheres; and micropumps and other chambered microdevices that can be used as a delivery system for a therapeutic agent. A microdevice generally is biologically inert, and can be biodegradable or excretable if desired. Various moieties, including microcapsules and microspheres, which can contain a therapeutic agent, and methods for linking a moiety or chambered microdevice to a peptide of the invention are well known in the art and commercially available (see, for example, "Remington's Pharmaceutical Sciences" 18th ed. (Mack Publishing Co. 1990), chapters 89–91; Harlow and Lane, *Antibodies: A laboratory manual* (Cold Spring Harbor Laboratory Press 1988); see, also, Hermanson, supra, 1996). Additional examples of moieties are known to those skilled in the art and are intended to be included within the meaning of the term so long as they possess a biologically useful function when linked to a homing peptide of the invention.

In one embodiment, a moiety can be a therapeutic agent. Thus, the invention provides a conjugate containing a heart homing peptide of the invention linked to a therapeutic agent.

A therapeutic agent is any agent that, when linked to a homing peptide of the invention, exerts a biologically useful function when targeted to heart, ischemic tissue or peripheral vasculature of the limbs. For example, a therapeutic agent can be a small organic molecule that, upon binding to a target cell via a linked heart homing peptide is internalized by the cell where it can effect its function. Particularly useful therapeutic agents include viral gene therapy vectors and viruses; nucleic acid molecules and oligonucleotides including antisense and dominant negative molecules; polypeptides and peptides; and small molecule drugs.

A conjugate of the invention can be particularly useful in treating atherosclerosis, which, with its consequences, constitutes the most common and important cause of disease and death in the western world. Atherosclerosis, like other occlusive vascular disease, is characterized by the abnormal accumulation of vascular smooth muscle cells, inflammatory cells, and extracellular matrix proteins within the intimal space between the endothelial lining and the medial layer (neointima formation). In particular, damage to the endothelium allows entry of cholesterol-rich low-density lipoproteins (LDLs) into the intima. Lipid is taken up by macrophages in the intima, with excessive lipid accumulating in the intimal macrophages through a receptor-independent pathway that takes up oxidized LDL. Macrophages release lipid into the intima and secrete cytokines that stimulate proliferation. Intimal cells with features of myofibroblasts secrete collagen, causing the plaque to become fibrotic. As the lesion develops, there is pressure atrophy of the media, and the elastic lamina is disrupted. Further collagen secretion forms a dense fibrous cap to the plaque (fibrolipid plaque), which contains free lipid as well as lipid in macrophages. Collagenization weakens the arterial wall, and the fragile endothelium often ulcerates, allowing platelet aggregation and thrombosis. Growth factors such as platelet-derived growth factor (PDGF) cause further plaque development by stimulating cell proliferation.

As set forth above, increased proliferation of intimal smooth muscle cells, resulting in myointimal hyperplasia and luminal narrowing, is a characteristic of the early phase of atherosclerosis. The abnormal cell proliferation which plays a role in neointima formation can be a consequence of specific growth factors such as platelet derived growth factor (PDGF), transforming growth factor-$\beta$1 (TGF-$\beta$1) or angiotensin II (Ang II) (Ross, *Annu. Rev. Physiol.* 57:791 (1995); Schwartz et al., *Circ. Res.* 77:445 (1995); and Gibbons and Dzau, *N. Eng. J. Med.* 330:1431 (1994)).

For treatment of atherosclerosis, a therapeutic agent can be a growth inhibitory agent that reduces or prevents vascular disease by limiting neointimal smooth muscle cell proliferation. For example, a herpes virus thymidine kinase (tk) gene and systemic ganciclovir can be used to kill proliferating cells and limit neointimal formation. In one study, porcine iliofemoral arteries were infected with an adenoviral vector encoding tk and, after exposure to ganciclovir, the neointimal thickening seen following balloon injury was reduced by 50–87% (Ohno et al., *Science* 265:781–784 (1994); see, also, Guzman et al., *Proc. Natl. Acad. Sci. USA* 91:10732–10736 (1994); Chang et al., *Mol. Med.* 1:172–181 (1995); and Simari et al., *Circulation* 92:1–501 (1995)). Thus, a heart homing peptide of the invention can be linked to a cytotoxic or cytostatic agent such as a thymidine kinase gene.

Additional therapeutic agents for limiting neointimal formation also are known in art and include genes that inhibit cell cycle proteins and proto-oncogenes (Simari and Nabel, *Semin. Intervent. Cardiol.* 1:77–83 (1996)). Such therapeutic agents include, for example, tumor suppressor genes such as p53 or retinoblastoma as well as genes encoding bcl-x, mutant forms of ras and nitric oxide synthetase. For example, the retinoblastoma gene product (Rb) inhibits cell proliferation in many mammalian cell types, and transfer of a recombinant adenovirus encoding active Rb into injured rat carotid and porcine iliac arteries resulted in decreased neointimal formation (Chang et al., *Science* 267:518–522 (1994)). Gene transfer of p53 similarly has been shown to inhibit vascular smooth muscle cell proliferation (Yonemitsu et al., *Circ. Res.* 82:147–156 (1998); see, also, Muller, *Prog. Cardiovas. Dis.* 40:117–128 (1997)). Direct gene transfer of dominant negative ras variants also inhibited intima development following balloon injury in rat carotid and porcine iliofemoral models (Chang et al., *J. Clin. Invest.* 96:2260–2268 (1995)). In a rat carotid injury model, gene transfer of nitric oxide synthetase also limited intimal formation (von der Leyen et al., *Proc. Natl. Acad. Sci., USA* 92:1137–1141 (1995). Additional cytotoxic or cytostatic agents that can be linked to a heart homing peptide of the invention include pro-apoptotic agents such as bcl-x (Pollman et al., *Nature Med.* 2:222–227 (1998))

A decoy or antisense oligonucleotide against a cellular target such as E2F or one of various cyclins also can be linked to a heart homing peptide of the invention and used to limit neointima proliferation (Morishita et al., *Circ. Res.* 82:1023–1028 (1998); and Mann et al., *Circulation* 96:1–4 1997)). The growth arrest homeobox gene gax, which is rapidly downregulated in vascular smooth muscle cells after vascular injury in vivo also can be linked to a heart homing peptide of the invention for use in inhibiting intimal hyperplasia (Smith et al., *Genes Dev.* 11:1674–1689 (1997); and Skopicki et al., *Circ. Res.* 80:452–462 (1997)). Additional therapeutic agents that can be useful in limiting intimal hyperplasia when linked to a peptide of the invention also are known in the art (see, for example, Laitinen and Yl ä-Herttuala, *Current Opin. Lipid.* 9:465–469 (1998).

Calcium antagonists, also known as calcium channel blockers (CBBs), have beneficial effects in many cardiovascular diseases and act as potent inhibitors of smooth muscle cell proliferation and migration. Additional properties that make these agents useful in treating atherosclerosis include inhibition of calcium influx into the vascular wall; reduction of extracellular matrix synthesis; promotion of uptake and breakdown of low-density lipoproteins; protection of lipoproteins from oxidative modification; maintenance of endothelial cell function; and inhibition of platelet activation. Among the calcium antagonists, amlodipine is a particularly useful therapeutic agent due to its vascular selectivity (Marche et al., *Int. J. Cardiol.* 62(Suppl.):S17–S22 (1997); Schachter, *Int. J. Cardiol.* 62(Suppl.):S85–S90 (1997)). Additional calcium antagonists that can be linked to a heart homing peptide of the invention include, for example, nicardipine, nifedipine, propanolol, isosorbide dinitrate, diltiazem, and isradipine (Nayler (Ed.) *Calcium Antagonists* pages 157–260 London: Academic Press (1988); Schachter, *Int. J. Cardiol.* 62(Suppl.):S9–S15 (1997)). Agents that elevate cAMP or cGMP content reduce vascular smooth muscle cell responsiveness or proliferation and also can be useful when linked to a heart homing peptide of the invention. Such agents include the cAMP phosphodiesterase inhibitor cilostasol and endothelium-derived nitric oxide (NO) or NO-generating vasodilators (Takahashi et al., *J. Cardiovas. Pharm.* 20:900–906 (1992); Cornwell et al., *Am. J. Physiol.* 267:C1405–1413 (1994)).

Angiogenesis-based therapy using an agent that stimulates new blood vessel formation (angiogenesis) also can be used to treat ischemic heart disease, for example, chronic myocardial ischemia or acute myocardial infarction (Ware and Simons, *Nature Med.* 3:158–164 (1997)). Many patients with severe vascular disease that are not candidates for mechanical revascularization can benefit from angiogenesis-based therapy, including those patients with occlusion of vessels too small to be bypassed, those without conduits and those who are not surgical candidates because of concomitant disease. It has been calculated that 314 million disease cases in the U.S. and European Union may benefit from angiogenesis-based therapy (Miller and Abrams, *Gen. Engin. News* 18:1 (1998)). Thus, a heart homing peptide of the invention can be linked to an agent that stimulates angiogenesis (angiogenic agent).

An angiogenic agent to be linked to a heart homing peptide can be a naturally occurring angiogenic growth factor or cytokine that induces or promotes angiogenesis by stimulating endothelial cell growth or migration. The angiogenic agent vascular endothelial growth factor (VEGF), also known as vascular permeability factor (VPF), is a key regulator of angiogenesis that stimulates endothelial cell proliferation and increases endothelial permeability without similar stimulation of smooth muscle cells. (Dvorak et al., *Am. J. Pathol.* 146:1029–1039 (1995); Thomas et al., *J. Biol. Chem.* 271:603–606 (1996); Olofsson et al., *Proc. Natl. Acad. Sci. USA* 93:2576–2581 (1996); and Joukov et al., *EMBO J.* 15:290–298 (1996); Harada et al., *Am. J. Physiol.* 270:H1791–H1802 (1996)). Transfer of plasmid DNA encoding VEGF has been shown to result in significant reduction in thrombus formation and intimal thickening following stent implantation (*J. Am. Coll. Cardiol.* 29:1371–1379 (1997)). An angiogenic agent can be, for example, a recombinant 165 kDa isoform of VEGF, designated rhVEGF, developed by Genentech; a nucleic acid molecule encoding the 121 amino acid isoform of VEGF (BioByPass™; GenVec/Parke Davis); or a nucleic acid encoding VEGF-2 (Vascular Genetics, Inc.). See, for example, Miller and Abrams, supra, 1998.

An angiogenic agent also can be a member of the fibroblast growth factor (FGF) family such as FGF-1 (acidic), FGF-2 (basic), FGF-4 or FGF-5, and in particular, FGF-2 (Slavin et al., *Cell Biol. Int.* 19:431–444 (1995); Folkman and Shing, *J. Biol. Chem.* 267:10931–10934 (1992)). An FGF angiogenic agent to be linked to a heart homing peptide of the invention can be, for example, FIBLAST™ (trafermin), a recombinant form of FGF-2 being developed by Scios, Inc. (Mountain View, Calif.) and Wyeth Ayerst Laboratories (Radnor, Pa.), or GENERX™, or an adenoviral gene therapy vector encoding FGF-4 developed by Collateral Therapeutics (San Diego, Calif.) and Schering AG (Miller and Abrams, supra, 1998).

An angiogenic agent also can be angiopoietin-1, an angiogenic factor that signals through the endothelial cell-specific Tie2 receptor tyrosine kinase (Davis et al., *Cell* 87:1161–1169 (1996)). Like VEGF, angiopoietin-1 is essential for normal vascular development, and its overexpression leads to increased angiogenesis (Suri et al., *Cell* 87:1171–1180 (1996)).

An angiogenic agent can be delivered, for example, as a protein as described in Harada et al., *J. Clin. Invest.* 94:623–630 (1994). Microspheres, for example, microspheres of 7 $\mu$m diameter to which an angiogenic factor such as bFGF is reversibly adsorbed through $SO_3$ residues, also can be linked to a heart homing peptide of the invention to selectively deliver the microspheres to the heart. Such microspheres lodge in the peripheral microcirculation without interfering with total flow and are slowly released over a period of a week (Arras et al., *Nature Biotech*. 16:159–162 (1998); see, also, Tice and Staas, *Nature Biotech*. 16:134 (1998)). A single injection of a biodegradable microsphere can be used to deliver an angiogenic factor that is released over one or several months following the injection, with the rate and duration of drug release controlled by factors such as the polymer type and microparticle size (Maulding, *Controlled Release* 6:167–176 (1987); Tice and Tabibi, pages 315–339 in Kydonieus (Ed.), *Treatise on Controlled Drug Delivery* Marcel Dekker, New York (1992)). A gene therapy vector also can be linked to a peptide of the invention to deliver an angiogenic factor such as VEGF or FGF-5 (see, for example, Isner et al., *Lancet* 348:370–374 (1996); Giordano et al., *Nature Med*. 2:534–539 (1996))

A therapeutic agent to be linked to a heart homing peptide of the invention also can be an antiviral or antibiotic agent. Numerous studies have reported an association of coronary atherosclerosis and restenosis with particular bacterial and viral infections, especially cytomegalovirus and *Chlamydia pneumoniae* (Cheng and Rivera, *Annals of Pharmacotherapy* 32:1310–1316 (1998)). For prophylactic use in a patient at high risk of developing atherosclerosis, such as a heart transplant patient, the patient is administered a conjugate of a heart homing peptide linked to an antiviral agent such as ganciclovir. Additional antiviral agents that can be linked to a heart homing peptide of the invention include, for example, Ribavirin (Virazole, 1-β-D-ribofuranosyl-1,2,4-triazole-3-carboximide) and recombinant human leukocyte IFN-α A/D (Matsumori et al., *Circulation* 71:834–839 (1985); Matsumori et al., *J. Am. Coll. Cardiol*. 9:1320–1325 (1987)).

Congestive heart failure (CHF), which affects nearly five million people in the United States alone, results when the heart is damaged from atherosclerosis or other conditions such as high blood pressure, myocardial infarction or defective heart valves. The failing heart works inefficiently, causing fluid retention, shortness of breath and fatigue. A heart homing peptide of the invention can be linked to a therapeutic agent for treatment of congestive heart failure, for example, a TNF inhibitor such as the recombinant soluble TNF decoy receptor, Embrel™ (Immunex Corp.; Seattle, Wash.).

Endothelins, polypeptides that constrict blood vessels, also are elevated in congestive heart failure. Thus, a heart homing peptide of the invention can be linked to a therapeutic agent that is an endothelin inhibitor, for example, the small molecule drug, TBC11251. This drug, which was developed by Texas Biotechnology Corp. and inhibits endothelin A-receptor binding and promotes relaxation of smooth muscle cells, has resulted in significant improvement in patients with moderate to severe congestive heart failure (Potera, *Gen. Engin. News* 18:12 (1998)).

A heart homing peptide of the invention also can be linked to a therapeutic agent that is an angiotensin-converting enzyme (ACE) inhibitor. Such an ACE inhibitor can be, for example, Natrecor (nesiritide; Scios, Inc.), which is a recombinant form of the cardiac hormone, b-type natriuretic peptide, which is produced primarily in the left ventricle of the heart and is released when the heart fails. By ridding the body of salt and water, dilating blood vessels and decreasing other hormones that raise blood pressure, Natrecor improved heart function, as demonstrated in a clinical study with 127 patients with congestive heart failure (Potera, supra, 1998).

A heart homing peptide also can be linked to a therapeutic agent for treatment of a cardiac arrhythmia, which is a disorder in which the normal periodicity and regular electromechanical activity of the heart is disrupted. Thus, in a conjugate of the invention, a therapeutic agent can be a well known antiarrhythmic agent such as a local anesthetic (class I agent), sympathetic antagonist (class II agent), antifibrillatory agent (class III agent) calcium channel agent (class IV agent) or anion antagonist (class V agent) as described in Vukmir, *Am. J. Emer. Med*. 13:459–470 (1995); Grant, *PACE* 20:432–444 (1997); AβMann, *Curr. Med. Res. Opin*. 13:325–343 (1995); and Lipka et al., *Am. Heart J*. 130:632–640 (1995). An antiarrhythmic agent that is a local anesthetic acts as fast sodium channel antagonist; such an antiarrhythmic agent can be, for example, procainamide, quinidine or disopyramide; lidocaine, phenytoin, tocainide or mexiletine; or encainide; flecainide; lorcainide; propafenone (III) or moricizine (Vukmir, supra, 1995). An antiarrhythmic agent also can be synpathetic antagonist (β-adrenergic antagonist) such as propranolol, esmolol, metoprolol, atenelal, or acebutolol or an antifibrillatory agent that acts by prolonging the action potential duration (APD), for example, bretylium, amiodarone, sotalol (II) or N-acetylprocainamide (Vukmir, supra, 1995). Additional antiarrhythmic agents that can be linked to a heart homing peptide of the invention include calcium channel agents such as verapamil, diltiazem, and bepridil, and anion antagonists such as alinidine (Vukmir, supra, 1995). The skilled person understands that these and other antiarrhythmic drugs known in the art can be useful in treating cardiac arrhythmias when linked to a heart homing peptide of the invention.

A therapeutic moiety useful in the invention also can be an anti-thrombotic agent that prevents the formation of a thrombus, which is an aggregation of blood factors, primarily platelets and fibrin with entrapment of cellular elements. Thrombus formation is stimulated by the presence of atheromatous plaques and is the main cause of episodes of acute ischemic heart disease. An anti-thrombotic agent useful in the invention can be, for example, an inhibitor of the IIb/IIIa integrin (Coller, *Circulation* 92:2373 (1995); a tissue factor inhibitor; or an anti-thrombin agent.

A heart homing peptide of the invention also can be linked to a therapeutic agent for treatment of restenosis, which is the re-narrowing of lumen dimensions which follows angioplasty, a procedure in which a balloon is inserted into an occluded vessel and then inflated to dilate the area of narrowing. Restenosis, which occurs in about 30 to 50% of cases over a time course of three to six months, involves cellular hyperplasia within the neointima, the organization of thrombus within the vessel wall and shrinkage of overall vessel dimensions. Angioplasty denudes the vessel of endothelial cells that would normally generate paracrine inhibitors of vascular smooth muscle migration and proliferation, such as nitric oxide. In addition, a deficiency in nitric oxide is associated with impaired vasorelaxation and increased adhesiveness, predisposing vascular tissue to atherosclerotic lesion formation (Gibbons and Dzau, *Science* 272:689–693 (1996)). Thus, a therapeutic agent for treatment of restenosis can be an endothelial cell-type nitric oxide (NO) synthase agent, which is an agent that enhances NO synthase activity.

A therapeutic NO synthase agent that is linked to a heart homing peptide of the invention can be, for example, a NO synthase gene or NO-donor drug. Transfection of a NO synthase gene into the vessel wall after balloon injury in a rat model of neointima formation resulted in the generation of NO and a substantial inhibition in the cell proliferation, migration and matrix production required for neointima formation (von der Leyen et al., supra, 1995). Clinical studies also indicate that a NO-donor drug can be used to augment NO activity and treat restenosis (Ferguson, *Circulation* 90:4 (1994)).

A heart homing peptide of the invention also can be used to target a therapeutic agent that is a replacement gene therapy vector for an inherited heart disease. Such an inherited disease can be, for example, an inherited disease of the myocardium such as X-linked dilated cardiomyopathy, hypertrophic cardiomyopathy or Long QT Syndrome or another disease for which the disease-causing mutation has been identified. (Bowles et al., *Cardiovas. Res.* 35:422–430 (1997)). Preferably, a heart homing peptide of the invention is linked to an adenoviral gene therapy vector for expression of the replacement gene in myocardium.

The present invention provides methods of treating a cardiovascular disease in a subject by administering a conjugate which contains a heart homing peptide linked to a therapeutic agent, where the heart homing peptide contains the amino acid sequence GGGVFWQ (SEQ ID NO: 2); HGRVRPH (SEQ ID NO: 3); VVLVTSS (SEQ ID NO: 4); CLHRGNSC (SEQ ID NO: 9) or CRSWNKADNRSC (SEQ ID NO: 10), or a functionally equivalent modification thereof. The methods of the invention are useful for treating a variety of cardiovascular diseases including atherosclerosis and restenosis.

A variety of cardiovascular diseases can be treated according to a method of the invention. Such cardiovascular diseases include, for example, atherosclerosis; thrombosis; restenosis; vasculitis including autoimmune and viral vasculitis such as polyarteritis nodosa, Churg-Strass syndrome, Takayasu's arteritis, Kawasaki Disease and Rickettsial vasculitis; atherosclerotic aneurisms; myocardial hypertrophy; congenital heart diseases (CHD); ischemic heart disease and anginas; acquired vavular/endocardial diseases; primary myocardial diseases including myocarditis; arrhythmias; and cardiac tumors. Cardiovascular diseases to be treated according to a method of the invention also include metabolic myocardial diseases or myocardiomyopathies such as congestive, hypertrophic or restrictive cardiomyopathies.

Further provided by the invention are methods of treating ischemic disease in a subject by administering a conjugate including an ischemic tissue selective peptide that selectively homes to ischemic tissue, where the peptide is linked to a moiety. A particularly useful moiety for treating ischemic disease is an angiogenic agent, examples of which are described hereinabove.

One skilled in the art would know that a conjugate of the invention can be administered to a subject by various routes including, for example, orally or parenterally, such as intravenously. The conjugate can be administered by injection or by intubation. A particularly useful conjugate is one in which a homing peptide such as a heart homing peptide or ischemic tissue selective peptide is linked to a moiety such as a liposome or other polymer matrix, which can have a drug or other therapeutic agent incorporated therein (Gregoriadis, *Liposome Technoloay*, Vol. 1 (CRC Press, Boca Raton, Fla. 1984)). Liposomes, for example, which consist of phospholipids or other lipids, are nontoxic, physiologically acceptable and metabolizable carriers that are relatively simple to make and administer.

Where a cardiovascular disease or ischemic disease is to be treated using gene therapy, a variety of methodologies are known in the art (see, for example, Li et al., *Cardiol.* 41:39–46 (1997)). Viral vectors, including retroviral and adenoviral vectors, can be particularly useful for gene delivery when linked to a heart homing peptide of the invention. In particular, replication deficient recombinant adenoviral vectors can be particularly useful for expression of a therapeutic gene in cardiac tissue. Additional methodologies for gene delivery to the heart or to ischemic tissue include hydrophilic polymers and cationic liposomes. See, for example, Simari and Nabel, supra, 1996; and Indolfi and Chiariello, *Cardiologia* 43:365–373 (1998)).

An effective amount of a conjugate of the invention is administered to the subject. An "effective amount" is the amount of the conjugate that produces a desired effect. An effective amount will depend, for example, on the moiety linked to the heart homing peptide or ischemic tissue selective peptide and on the intended use. An effective amount of a particular conjugate for a specific purpose can be determined using methods well known to those in the art.

Where a conjugate of the invention is to be administered orally, a homing peptide of the invention can be chemically modified to render it less susceptible to degradation by endogenous proteases or more absorbable through the alimentary tract (see, for example, Ecker and Crooke, *Biotechnology* 13:351–360 (1995), and Blondelle et al., *Trends Anal. Chem.* 14:83–92 (1995), and the references cited therein; see, also, Goodman and Ro, *Peptidomimetics for Drug Design*, in "Burger's Medicinal Chemistry and Drug Discovery" Vol. 1 (ed. M. E. Wolff; John Wiley & Sons 1995), pages 803–861). In addition, a homing peptide of the invention or peptide or polypeptide therapeutic agent linked thereto can be modified to be suitable for oral administration by including one or more D-amino acids or can be a peptidomimetic or peptoid such as a vinylogous peptoid.

When administered to a subject, a conjugate of the invention generally is delivered as a pharmaceutical composition containing, for example, the conjugate and a pharmaceutically acceptable carrier. Such carriers are well known in the art and include, for example, aqueous solutions such as water or physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of the complex. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition.

The invention also provides a conjugate containing a homing peptide linked to a detectable agent. Such a detectable agent can be, for example, a radionuclide or an imaging agent, which allows detection or visualization of a tissue such as the heart. The type of detectable agent selected will depend upon the application. For example, for an in vivo diagnostic imaging study, a heart homing peptide can be linked to a diagnostic agent that, upon administration to the subject, is detectable external to the subject. Such a detectable agent can be, for example, a gamma ray emitting radionuclide such as indium-113, indium-115 or technetium-99, which, following administration to a subject, can be visualized using a solid scintillation detector. The ability to image or visualize the heart can provide a means to diagnose cardiovascular disease. The presence of cardiovascular disease can be revealed by detecting that a region of the heart does not contain the conjugate, thus indicating an abnormality in circulation to the region, or by detecting that the heart is, for example, abnormally enlarged. Similarly, the presence of ischemic disease can be revealed by detecting a signal from an ischemic tissue selective peptide linked to a detectable agent.

A particularly useful detectable agent can be a diagnostic contrast agent such as the ultrasound contrast agent IMAGENT (Alliance Pharmaceuticals; San Diego, Calif.). For example, when linked to a heart homing peptide of the invention, such a diagnostic contrast agent can be used to enhance ultrasound images to aid in the assessment of heart function and perfusion, and in detection of tumors or blood flow abnormalities.

A detectable agent also can be an agent that facilitates detection in vitro. For example, a conjugate containing a heart homing peptide or ischemic tissue selective peptide linked to an enzyme can be used to produce a visible signal when an appropriate substrate is present. Such a conjugate, which can include, for example, alkaline phosphatase or luciferase or the like, can be useful in a method such as immunohistochemistry. Such a conjugate can be used to detect the presence of a target molecule to which the homing peptide binds, for example, during purification of the target molecule.

A heart homing peptide or ischemic tissue selective peptide disclosed herein also can be useful for identifying the presence of a target molecule, particularly a cell surface protein, that is recognized by the homing peptide, and for substantially isolating the target molecule. Thus, the invention provides methods of identifying target molecules that selectively bind a homing peptide of the invention. Such methods involve contacting a sample with a homing peptide and detecting selective binding of a component of a sample, wherein such binding identifies the presence of a target molecule.

As used herein, the term "sample" is used in its broadest sense to mean a cell, tissue, organ or portion thereof that is isolated from the body. A sample can be, for example, a histologic section of cardiac tissue or a specimen obtained by biopsy or cardiac cells that are placed in or adapted to tissue culture. If desired, a sample can be processed, for example, by homogenization, which can be an initial step for isolating the target molecule to which a homing peptide binds.

In one embodiment, a conjugate of the invention contains a homing peptide of the invention linked to a tag. As used herein, the term "tag" means a physical, chemical or biological moiety, such as an insoluble support such as a chromatography matrix, or a molecule such as biotin, hemagglutinin antigen, polyhistidine, T7 or another molecule known in the art. Methods for tagging a molecule are well known in the art (Hermanson, *Bioconjugate Techniques*, (Academic Press 1996)). The link between a heart homing peptide and a tag can be a covalent or a non-covalent bond and, if desired, the link can be selectively cleavable. A conjugate containing a tag can be useful to isolate a target molecule to which a homing peptide such as a heart homing peptide binds.

A tag also can serve as a support. As used herein, the term "support" means a tag having a defined surface to which a peptide can be attached. A support can be, for example, a biological tag such as a virus or virus-like particle such as a bacteriophage ("phage"); a bacterium such as *E. coli*; or a eukaryotic cell such as a yeast, insect or mammalian cell; or can be a physical tag such as a liposome or a microbead, which can be composed of a plastic, agarose, gelatin or other biological or artificial material. If desired, an appropriate spacer can be positioned between the peptide and the support such that the ability of the heart homing peptide to interact with the target molecule is not hindered. A spacer molecule also can contain a reactive group, which provides a convenient and efficient means of linking a molecule to a support (see Hermanson, supra, 1996).

A particularly useful conjugate contains a homing peptide linked to a solid support such as a chromatography matrix. Such an immobilized peptide can be used for affinity chromatography by passing an appropriately processed sample of cardiac tissue or ischemic tissue over a column containing the matrix under conditions that allow specific binding of the homing peptide to the particular target molecule (see, for example, Deutscher, *Meth. Enzymol.*, Guide to Protein Purification (Academic Press, Inc., ed. M. P. Deutscher, 1990), Vol. 182; see pages 357–379). Unbound and nonspecifically bound material can be removed; subsequently, the target molecule can be eluted from the column, collected in substantially isolated form and characterized using well known methods.

As an alternative to using a sample of cardiac tissue or ischemic tissue for identifying a target molecule, extracts of cultured cells derived from heart tissue or ischemic tissue, or extracts of cultured endothelial cells can be used as the starting material. Selection of cells containing the target molecule can be determined using binding and cell attachment assays (see Barry et al., *Nature Med.* 2:299–305 (1996)). Those cells containing the target molecule can be used to prepare extracts for isolation and identification of a target molecule, as described above.

Upon identifying an appropriate cell line expressing the target molecule, the target molecule can be labeled by growing the cells in medium containing radiolabeled amino acids. The radiolabeled amino acids are incorporated into the target molecule, thus facilitating its identification during purification. Labeled cells can be extracted, for example, with octylglucoside, and the extract subsequently fractionated by affinity chromatography using a heart homing peptide of the invention coupled to a matrix such as SEPHAROSE. Extracts prepared from human umbilical vein endothelial cells, for example, can be used as a control. The purified target molecule then can be microsequenced and antibodies prepared. If desired, oligonucleotide probes can be prepared and used to isolate cDNA clones encoding the target receptor. Alternatively, an anti-receptor antibody can be used to isolate a cDNA clone from an expression library (see Argraves et al., *J. Cell Biol.* 105:1183–1190 (1987)).

In addition to biochemically isolating a target molecule, a nucleic acid encoding the target molecule can be isolated by using a heart homing peptide of the invention as a chemical probe to screen a cDNA expression library prepared, for example, from cardiac RNA for clones that express the target molecule. For example, bacteria expressing a cardiac cDNA library can be attached to a membrane, lysed, and screened with a heart homing peptide conjugated, for example, to an enzyme that produces a calorimetric or fluorescent signal. After bacterial clones expressing a target molecule are identified, the cDNA encoding the target molecule is isolated.

A mammalian cell expression cloning system such as the COS cell system also can be used to identify a target molecule. For example, a cDNA library prepared using mRNA from ischemic or normal primary cardiac cells can be cloned into a mammalian expression vector. Cells expressing a cDNA encoding the target molecule then can be selected using a heart homing peptide of the invention as a probe, for example, by panning of cell clones against a heart homing peptide attached to a plate. Alternatively, phage displaying the heart homing peptide can be attached to magnetic beads coated, for example, with anti-M13 antibodies (Pharmacia). Cells expressing a target molecule that binds to the heart homing peptide then can be recovered, and the plasmids encoding the receptor isolated. The recovered plasmid preparations can be divided into pools and examined in COS cell transfections. The procedure can be repeated until single plasmids are obtained that enable the COS cells to bind the heart homing peptide.

The following examples are intended to illustrate but not limit the present invention.

EXAMPLE I

IN VIVO PANNING FOR IDENTIFICATION OF PEPTIDES THAT SELECTIVELY HOME TO NORMAL HEART

This example describes the use of in vivo panning for identification of peptides that selectively home to normal heart tissue.

In vivo panning was performed to identify phage that selectively home to normal coronary endothelium by injection of phage libraries and isolation of individual phage from the heart as follows. Phage peptide libraries were constructed as described previously by Koivunen et al., *Biotechnology* 13:265–270 (1995), with the Fuse5 vector and K91Kan obtained from G. Smith (see, also, Koivunen et al., *Meth. Enzymol.* 245:346–369 (1994b)). Both linear ($X_7$ (SEQ ID NO: 1)) and cyclic ($CX_7C$ (SEQ ID NO: 13), $CX_9C$ (SEQ ID NO: 14), and $CX_{11}C$ (SEQ ID NO: 15)) libraries were used, where "C" indicates cysteine and "$X_N$" indicates the given number of individually selected amino acids. These libraries can display cyclic peptides when at least two cysteine residues are present in the peptide. The libraries were generated using oligonucleotides constructed such that "C" was encoded by the codon TGT and "$X_N$" was encoded by NNK, where "N" is equal molar mixtures of A, C, G and T, and where "K" is equal molar mixtures of G and T. Oligonucleotides were made double stranded by three cycles of PCR amplification, purified and ligated to the nucleic acid encoding the gene III protein in the Fuse5 vector such that, upon expression, the peptide is present as a fusion protein at the N-terminus of the gene III protein.

Libraries were administered independently with the initial titer of the various libraries. In vivo phage selection was performed as described in Pasqualini and Ruoslahti, *Nature* 380:364–366 (1996), with a few modifications. In both normal and ischemic targeting, $2.5 \times 10^8$ transducing units of the initial phage libraries were injected intravenously into the jugular vein. After 5 minutes of phage circulation in vivo, the heart was arrested by intraventricular injection of a hyperkalemic (30 mM KCl), hypothermic solution of DMEM, and the vasculature cleared of blood by perfusion with 5–10 ml of hyperkalemic DMEM through a left ventricular cannula. After the heart and brain were harvested, homogenized and weighed, phage were rescued by infection with K91 Kan bacteria. For the second and third rounds of selection, 200 normal or 100 ischemic clones were picked from the previous round and individually grown to saturation. Cultures were then pooled, phage particles purified and $10^{10}$ TU of a pool reinjected into similarly treated mice. Single stranded phage DNA from individual third round clones was prepared, and the inserts sequenced as described previously (Rajotte et al., *J. Clinical Invest.* 102:430–437 (1998)). Phage with sequences appearing multiple times were characterized further by individual injection into mice.

All data were calculated as the ratio of the number of phage obtained per gram of heart tissue to the number of phage obtained per gram of brain tissue. Means, standard deviations, standard errors and parametric statistics were based on the assumption that this ratio is derived from a log-normal distribution.

The results of in vivo panning to normal heart are shown in Table 1. Tetracycline resistant phage without a peptide insert (Fd-Tet) typically yielded one to four times more phage per gram of heart tissue than per gram of brain tissue (Table 1), and the unselected library also fell within this range. Subsequent rounds of screening in the normal heart showed approximately a two-fold enrichment.

TABLE 1

In Vivo Screening of Phage Libraries in
Normal and Ischemic/Reperfused Myocardium

| Screening | Phage $g^{-1}$ heart/ Phage $g^{-1}$ brain |
|---|---|
| Insertless Normal | 2.69 |
| Unselected Library | 2.08 |
| Round 2 | 5.50 |
| Round 3 | 6.70 |
| Ischemic/Reperfused | |
| Unselected Library | 1.37 |
| Round 2 | 0.78 |
| Round 3 | 1.43 |

TABLE 2

Sequences of heart homing phage and
relative enrichment (compared with insertless phage)

| SEQ ID NO: | Sequence | Targeted Tissue | Enrichment |
|---|---|---|---|
| 2 | GGGVFWQ | Normal Heart | 5-fold |
| 3 | HGRVRPH | Normal Heart | 2-fold |
| 4 | VVLVTSS | Normal Heart | 2-fold |
| 9 | CLHRGNSC | Normal Heart | 2-fold |
| 10 | CRSWNKADNRSC | Ischemic Heart | 5-fold |

Figure 1:
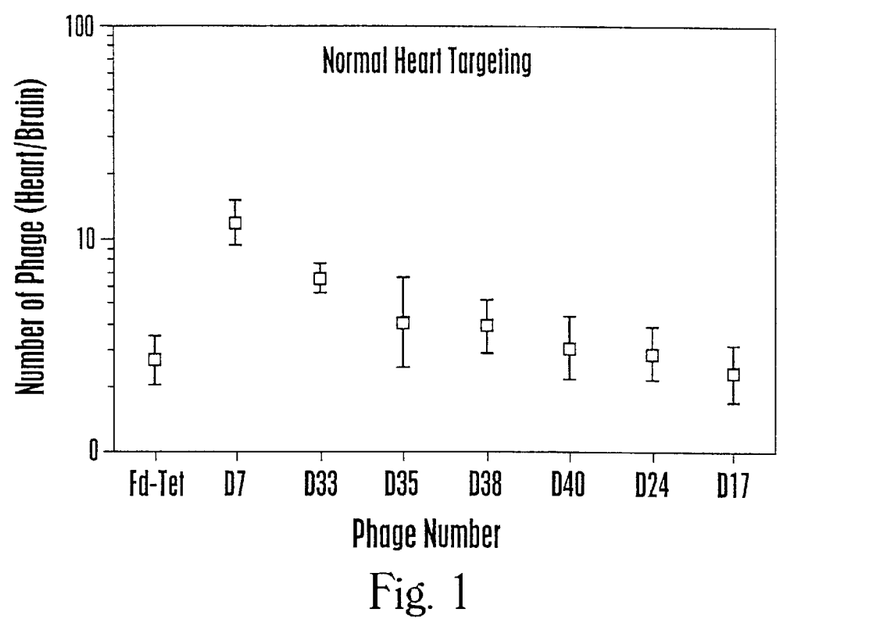

Several individual phage representing 4–6% of the total recovered sequences were tested individually in multiple animals (n=6 or 7). As shown in Table 2, phage bearing the sequence GGGVFWQ (SEQ ID NO: 2; D7) revealed strong (~5-fold) enrichment to the cardiac vasculature (p<0.002). In addition, phage bearing the sequence HGRVRPH (SEQ ID NO: 3; D33) and VVLVTSS (SEQ ID NO: 4; D35) had moderate (~2 fold) enrichment to the cardiac vasculature (see Table 2). Several other sequences demonstrated minimal homing to the heart (FIG. 1).

These results indicate that in vivo panning can be used to identify peptides that selectively home to the heart.

EXAMPLE II

IN VIVO PANNING FOR IDENTIFICATION OF PEPTIDES THAT SELECTIVELY HOME TO ISCHEMIC MYOCARDIUM

This example describes the use of in vivo panning for identification of peptides that selectively home to ischemic heart in preference to normal heart and other tissues.

In vivo panning was used to identify peptides that recognize cardiac endothelium altered by early myocardial ischemia-reperfusion injury. An ischemic period of 30 minutes followed by 30 minutes of reperfusion allowed some changes in the endothelium to occur while minimizing leukocyte adhesion and vascular plugging.

Ischemia-reperfusion was performed as follows using large male CD-1 mice weighing about 40 grams to facilitate the surgical protocol. Briefly, mice were anesthetized by an intramuscular injection of a mixture of xylazine (50 mg/kg) and ketamine (50 mg/kg) and subsequently intubated with an endotracheal tube and ventilated with a mixture of oxygen and room air using a Harvard Apparatus (0.05 ml; 100 bpm). The heart was exposed with a left thoracotomy, and a 7-0 suture was placed under the left anterior descending (LAD) coronary artery; the vessel was occluded by tying a knot over a small piece of polyethylene tubing (PE50). Ischemia was confirmed by cyanosis of the myocardium. After 30 minutes of occlusion, the knot was cut and blood flow restored to the region. Reperfusion was allowed to proceed for 30 minutes before phage targeting to allow for some vascular changes while limiting neutrophil recruitment to the area. Reperfusion was confirmed by injection of Evan's blue dye into the left ventricle and visualization of flow into the left anterior descending coronary artery.

In vivo selection was performed essentially as described in Example I. As shown in Table 1, three rounds of phage selection with the $CX_{10}C$, $CX_7C$ and $CX_6C$ libraries did not reveal enrichment in ischemic/reperfused myocardium compared to the unselected library. Nevertheless, phage clones representing 5–11% of the sequences were assayed individually for their accumulation in both normal and ischemic heart.

Figure 2:
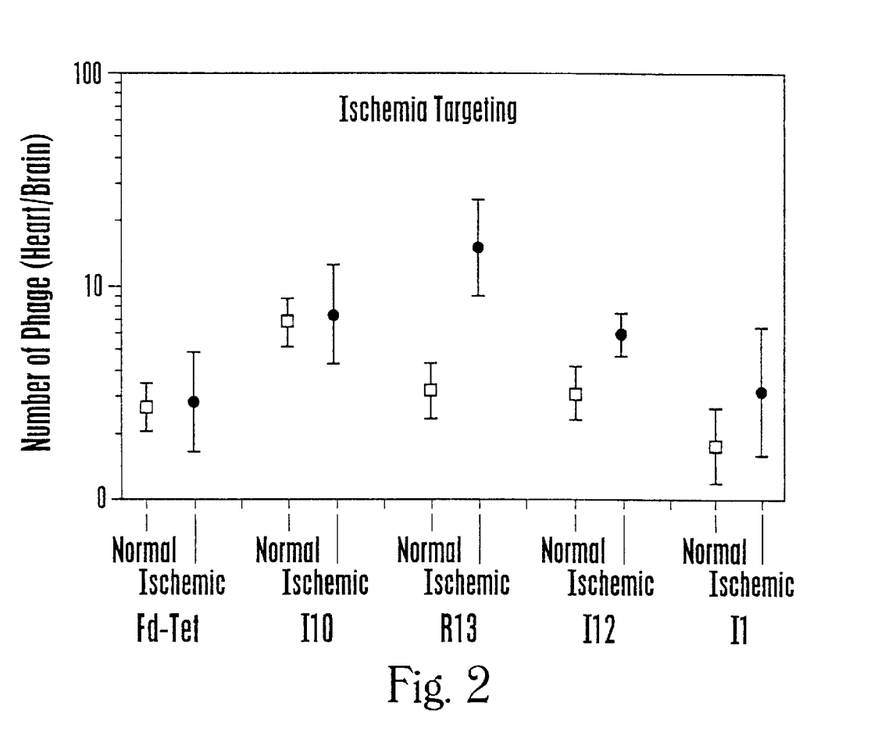

Insertless phage (Fd-tet) did not reveal increased homing to the ischemic myocardium, but in the individual experiments appeared to be more variable in their homing to ischemic heart as compared to normal heart (FIG. 2). Phage bearing the sequence CRSWNKADNRSC (SEQ ID NO: 10; R13) showed 5-fold enrichment in ischemic heart but did not target the normal heart (Table 2). In addition, phage bearing the sequence CLHRGNSC (SEQ ID NO: 9; I10), which had been selected as accumulating in ischemia-reperfusion injured myocardium, showed moderate (~2-fold) enrichment to ischemic myocardium as well as normal tissue, consistent with the expectation that some of the tissue subjected to ischemia-reperfusion is not injured. Two other phage tested appeared to have no preference for the normal myocardium with little or no preference for ischemic myocardium. These results suggest that homing of CRSWNKADNRSC (SEQ ID NO: 10; R13) and CLHRGNSC (SEQ ID NO: 9; I10) to ischemic myocardium was not due to trapping of the phage particles by neutrophils or vascular plugging.

Figure 3:
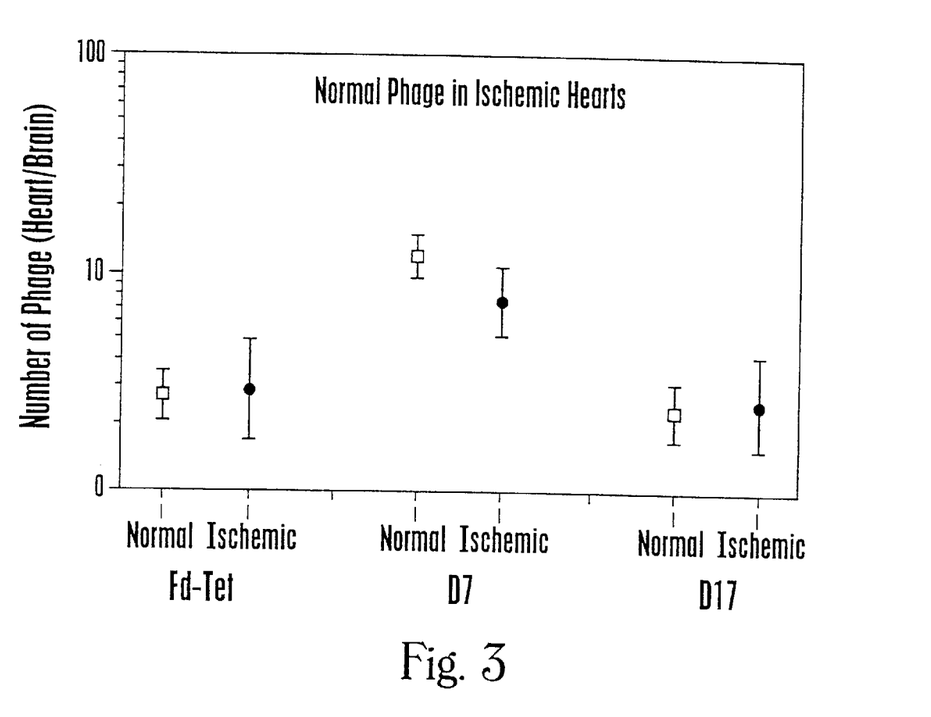
FIG. 3 shows targeting of individual phage identified by homing to normal heart (open squares) to ischemia-reperfusion injured myocardium (closed circles). The phage that strongly targeted the normal myocardium (SEQ ID NO: 2; D7) and one that clearly did not target the normal myocardium (SEQ ID NO: 8; D17) were tested for homing in ischemic-reperfused myocardium. The number of phage recovered from the heart (per gram) was normalized by the number of phage recovered from the brain (per gram). The data for the normal heart is the same as that presented in FIG. 1. The data shown are the logarithmic means and logarithmic standard errors for six to seven individual experiments.

Phage GGGVFWQ (SEQ ID NO: 2; D7), which binds to normal heart, as well as phage that did not home to normal heart (SEQ ID NO: 8; D17) were also assayed for their ability to home to ischemic/reperfused myocardium in order to further verify that phage accumulation in ischemic heart was not due to trapping of phage by dysfunctional endothelium. As shown in FIG. 3, the number of phage recovered from hearts subjected to ischemia-reperfusion injury remained enriched for the normal homing phage (p<0.001) while it did not change for the non-homing phage (p>0.6). As observed with the insertless phage, greater variance in the homing was seen for the ischemic myocardium.

Figure 4:
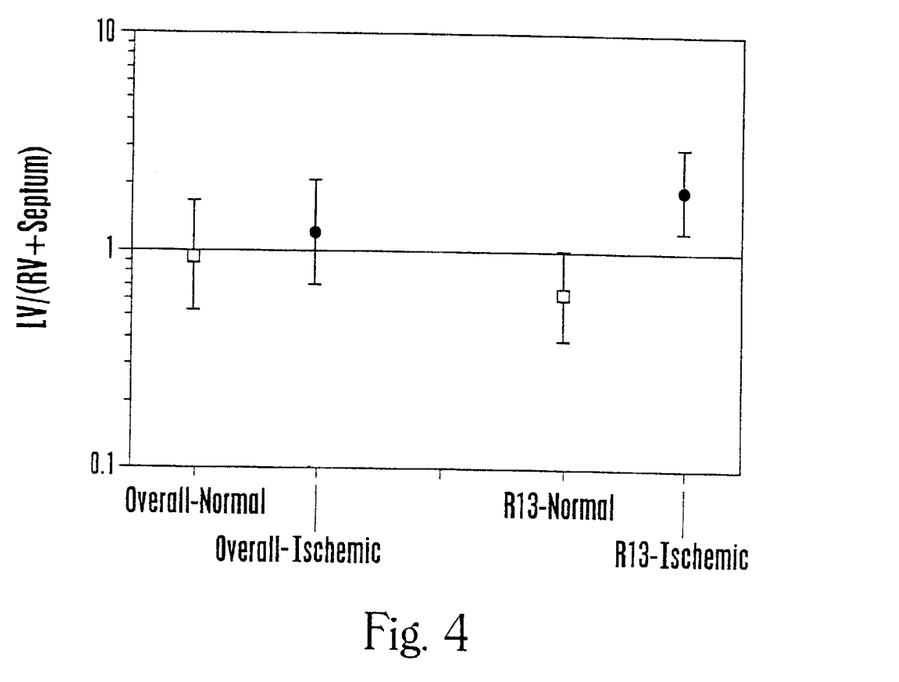
FIG. 4 shows preferential enrichment to injured left ventricular myocardium for phage selected for homing to ischemia-reperfusion injured myocardium. The number of phage recovered from the left ventricle ($g^{-1}$) was normalized by the number of phage recovered from the right ventricle and septum ($g^{-1}$). The overall data shown are a logarithmic mean and logarithmic standard deviation for 47 normal and 35 ischemic hearts. The data for phage bearing SEQ ID NO: 10 (R13) are for six individual animals each.

As a further test of specificity for homing to ischemic heart, phage homing to the injured left ventricle was compared to homing to the normal right ventricle and septum. In all of the ischemic hearts, and many of the normal hearts, the heart was divided into two parts: (1) left ventricular free wall and (2) ventricular septum plus right ventricle. In all of the normal hearts, the ratio of phage targeting the left ventricle to phage targeting the right ventricle and septum was on average 0.95 (FIG. 4). In normal hearts, a similar distribution was observed with phage bearing CRSWNKADNRSC (SEQ ID NO: 10; R13). In contrast, when SEQ ID NO: 10 was injected into animals that had undergone myocardial ischemia-reperfusion, more phage were recovered from the injured left ventricle than the right ventricle in each sample. When the ratio of phage accumulation in the left ventricle only is calculated relative to accumulation in the brain, the preferential accumulation of CRSWNKADNRSC (SEQ ID NO: 10; R13) phage is 7-fold compared with 5-fold enrichment for the heart in toto. This preferential homing to the ischemic left ventricle was not found for the other phage.

These results indicate that a heart homing peptide such as SEQ ID NO: 10 can selectively home to ischemic heart tissue without homing to normal tissue and can confer selective homing on a linked moiety such as a phage. These results further indicate that a heart homing peptide such as SEQ ID NO: 9 can target both ischemic and normal heart tissue.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

We claim:

1. An isolated heart homing peptide that selectively homes to cardiac tissue, comprising an amino acid sequence that has a length of less than 100 amino acids.

2. An isolated heart homing peptide that selectively homes to cardiac tissue, comprising an amino acid sequence selected from the group consisting of:
   GGGVFWQ (SEQ ID NO: 2);
   CLHRGNSC (SEQ ID NO: 9); and
   CRSWNKADNRSC (SEQ ID NO: 10), or a functionally equivalent peptiodomimetic thereof.

3. The isolated heart homing peptide of claim 2, having a length less than forty amino acids.

4. The isolated heart homing peptide of claim 2, having a length of less than fifteen amino acids.

5. The isolated heart homing peptide of claim 2, comprising the amino acid sequence GGGVFWQ (SEQ ID NO: 2), or a functionally equivalent peptidomimetic thereof.

6. The isolated heart homing peptide of claim 5, comprising the amino acid sequence GGGVFWQ (SEQ ID NO: 2).

7. The isolated heart homing peptide of claim 6, which is GGGVFWQ (SEQ ID NO: 2).

8. An isolated heart homing peptide that selectively homes to cardiac tissue, comprising the amino acid sequence HGRVRPH (SEQ ID NO: 3), or a functionally equivalent peptidomimetic thereof, wherein said peptide has a length of less than 100 amino acids.

9. The isolated heart homing peptide of claim 8, comprising the amino acid sequence HGRVRPH (SEQ ID NO: 3).

10. The isolated heart homing peptide of claim 9, which is HGRVRPH (SEQ ID NO: 3).

11. An isolated heart homing peptide that selectively homes to cardiac tissue, comprising the amino acid sequence VVLVTSS (SEQ ID NO: 4), or a functionally equivalent peptidomimetic thereof, wherein said peptide has a length of less than 200 amino acids.

12. The isolated heart homing peptide of claim 11, comprising the amino acid sequence VVLVTSS (SEQ ID NO: 4).

13. The isolated heart homing peptide of claim 12, which is VVLVTSS (SEQ ID NO: 4).

14. The isolated heart homing peptide of claim 2, comprising the amino acid sequence CLHRGNSC (SEQ ID NO: 9), or a functionally equivalent peptidomimetic thereof.

15. The isolated heart homing peptide of claim 14, comprising the amino acid sequence CLHRGNSC (SEQ ID NO: 9).

16. The isolated heart homing peptide of claim 15, which is CLHRGNSC (SEQ ID NO: 9).

17. The isolated heart homing peptide of claim 2, comprising the amino acid sequence CRSWNKADNRSC (SEQ ID NO: 10), or a functionally equivalent peptidomimetic thereof.

18. The isolated heart homing peptide of claim 17, comprising the amino acid sequence CRSWNKADNRSC (SEQ ID NO: 10).

19. The isolated heart homing peptide of claim 18, which is CRSWNKADNRSC (SEQ ID NO: 10).

20. An isolated peptide that selectively homes to ischemic tissue.

21. The isolated peptide of claim 20, which is a peptide comprising the amino acid sequence CRSWNKADNRSC (SEQ ID NO: 10), or a functionally equivalent peptidomimetic thereof.

22. The isolated peptide of claim 21, having a length of less than forty amino acids.

23. The isolated peptide of claim 21, having a length of less than fifteen amino acids.

24. The isolated heart homing peptide of claim 8, having a length of less than forty amino acids.

25. The isolated heart homing peptide of claim 8, having a length of less than fifteen amino acids.

26. The isolated heart homing peptide of claim 11, having a length of less than forty amino acids.

27. The isolated heart homing peptide of claim 11, having a length of less than fifteen amino acids.

* * * * *

SEQUENCE LISTING

```
<160> NUMBER OF SEQ ID NOS:  15

<210> SEQ ID NO 1
<220> FEATURE:
<223> OTHER INFORMATION: synthetic construct

<400> SEQUENCE: 1

000

<210> SEQ ID NO 2
<211> LENGTH: 7
```

```
<212> TYPE: PRT
<213> ORGANISM: Artificial Sequence
<220> FEATURE:
<223> OTHER INFORMATION: synthetic construct

<400> SEQUENCE: 2

Gly Gly Gly Val Phe Trp Gln
  1               5

<210> SEQ ID NO 3
<211> LENGTH: 7
<212> TYPE: PRT
<213> ORGANISM: Artificial Sequence
<220> FEATURE:
<223> OTHER INFORMATION: synthetic construct

<400> SEQUENCE: 3

His Gly Arg Val Arg Pro His
  1               5

<210> SEQ ID NO 4
<211> LENGTH: 7
<212> TYPE: PRT
<213> ORGANISM: Artificial Sequence
<220> FEATURE:
<223> OTHER INFORMATION: synthetic construct

<400> SEQUENCE: 4

Val Val Leu Val Thr Ser Ser
  1               5

<210> SEQ ID NO 5
<211> LENGTH: 7
<212> TYPE: PRT
<213> ORGANISM: Artificial Sequence
<220> FEATURE:
<223> OTHER INFORMATION: synthetic construct

<400> SEQUENCE: 5

Gln Gly Arg Leu Tyr Asn Tyr
  1               5

<210> SEQ ID NO 6
<211> LENGTH: 7
<212> TYPE: PRT
<213> ORGANISM: Artificial Sequence
<220> FEATURE:
<223> OTHER INFORMATION: synthetic construct

<400> SEQUENCE: 6

Ala Trp Gly Leu Ala Ser Tyr
  1               5

<210> SEQ ID NO 7
<211> LENGTH: 7
<212> TYPE: PRT
<213> ORGANISM: Artificial Sequence
<220> FEATURE:
<223> OTHER INFORMATION: synthetic construct

<400> SEQUENCE: 7

Arg Ser Met Pro Leu Leu Ser
  1               5

<210> SEQ ID NO 8
<211> LENGTH: 7
<212> TYPE: PRT
```

```
<213> ORGANISM: Artificial Sequence
<220> FEATURE:
<223> OTHER INFORMATION: synthetic construct

<400> SEQUENCE: 8

Arg Pro Gly Arg Leu Asn Gly
 1               5

<210> SEQ ID NO 9
<211> LENGTH: 8
<212> TYPE: PRT
<213> ORGANISM: Artificial Sequence
<220> FEATURE:
<223> OTHER INFORMATION: synthetic construct

<400> SEQUENCE: 9

Cys Leu His Arg Gly Asn Ser Cys
 1               5

<210> SEQ ID NO 10
<211> LENGTH: 12
<212> TYPE: PRT
<213> ORGANISM: Artificial Sequence
<220> FEATURE:
<223> OTHER INFORMATION: synthetic construct

<400> SEQUENCE: 10

Cys Arg Ser Trp Asn Lys Ala Asp Asn Arg Ser Cys
 1               5                  10

<210> SEQ ID NO 11
<211> LENGTH: 8
<212> TYPE: PRT
<213> ORGANISM: Artificial Sequence
<220> FEATURE:
<223> OTHER INFORMATION: synthetic construct

<400> SEQUENCE: 11

Cys Ser Met Tyr Phe Gln Arg Cys
 1               5

<210> SEQ ID NO 12
<211> LENGTH: 12
<212> TYPE: PRT
<213> ORGANISM: Artificial Sequence
<220> FEATURE:
<223> OTHER INFORMATION: synthetic construct

<400> SEQUENCE: 12

Cys Asn Ala Ser Ile Leu Arg Asn Gly Gln Asn Cys
 1               5                  10

<210> SEQ ID NO 13
<220> FEATURE:
<223> OTHER INFORMATION: synthetic construct

<400> SEQUENCE: 13

000

<210> SEQ ID NO 14
<220> FEATURE:
<223> OTHER INFORMATION: synthetic construct

<400> SEQUENCE: 14

000
```

-continued

```
<210> SEQ ID NO 15
<220> FEATURE:
<223> OTHER INFORMATION: synthetic construct

<400> SEQUENCE: 15

000
```